United States Patent [19]

Edelmann

[11] 4,232,453
[45] Nov. 11, 1980

[54] DEVICE FOR FREEZE DRYING AND SYNTHETIC RESIN IMPREGNATION WHEN NECESSARY OF SMALL BIOLOGICAL OBJECTS FOR ELECTRON MICROSCOPIC EXAMINATION

[75] Inventor: Ludwig Edelmann, Homburg, Fed. Rep. of Germany

[73] Assignee: C. Reichert Optische Werke, AG, Vienna, Austria

[21] Appl. No.: 945,372

[22] Filed: Sep. 25, 1978

[51] Int. Cl.³ .............................................. F26B 13/30
[52] U.S. Cl. ...................................... 34/92; 34/5; 62/268; 62/514 R
[58] Field of Search ............... 34/5, 92; 62/514 R, 62/100, 268

[56] References Cited

U.S. PATENT DOCUMENTS

| 2,163,996 | 6/1939 | Flosdorf | 34/5 |
| 3,009,258 | 11/1961 | Taylor | 34/92 |

Primary Examiner—John J. Camby
Attorney, Agent, or Firm—Jeremiah J. Duggan; Alan H. Spencer

[57] ABSTRACT

A tray for holding a biological specimen and a submersible container for freeze-drying the specimen are disclosed. A heating element to melt a synthetic resin for embedding the specimen is also disclosed.

13 Claims, 4 Drawing Figures

DEVICE FOR FREEZE DRYING AND SYNTHETIC RESIN IMPREGNATION WHEN NECESSARY OF SMALL BIOLOGICAL OBJECTS FOR ELECTRON MICROSCOPIC EXAMINATION

The invention concerns a device for the freeze drying and synthetic resin impregnation if necessary of small biological objects for electron microscopic examination, with a sample tray having at least one recess to accept an object, which is enclosed by a container which can be evacuated, and whose temperature can be controlled at a desired level by a cooling fluid and with an adjustable heating device connected with the sample tray.

Figure 1:
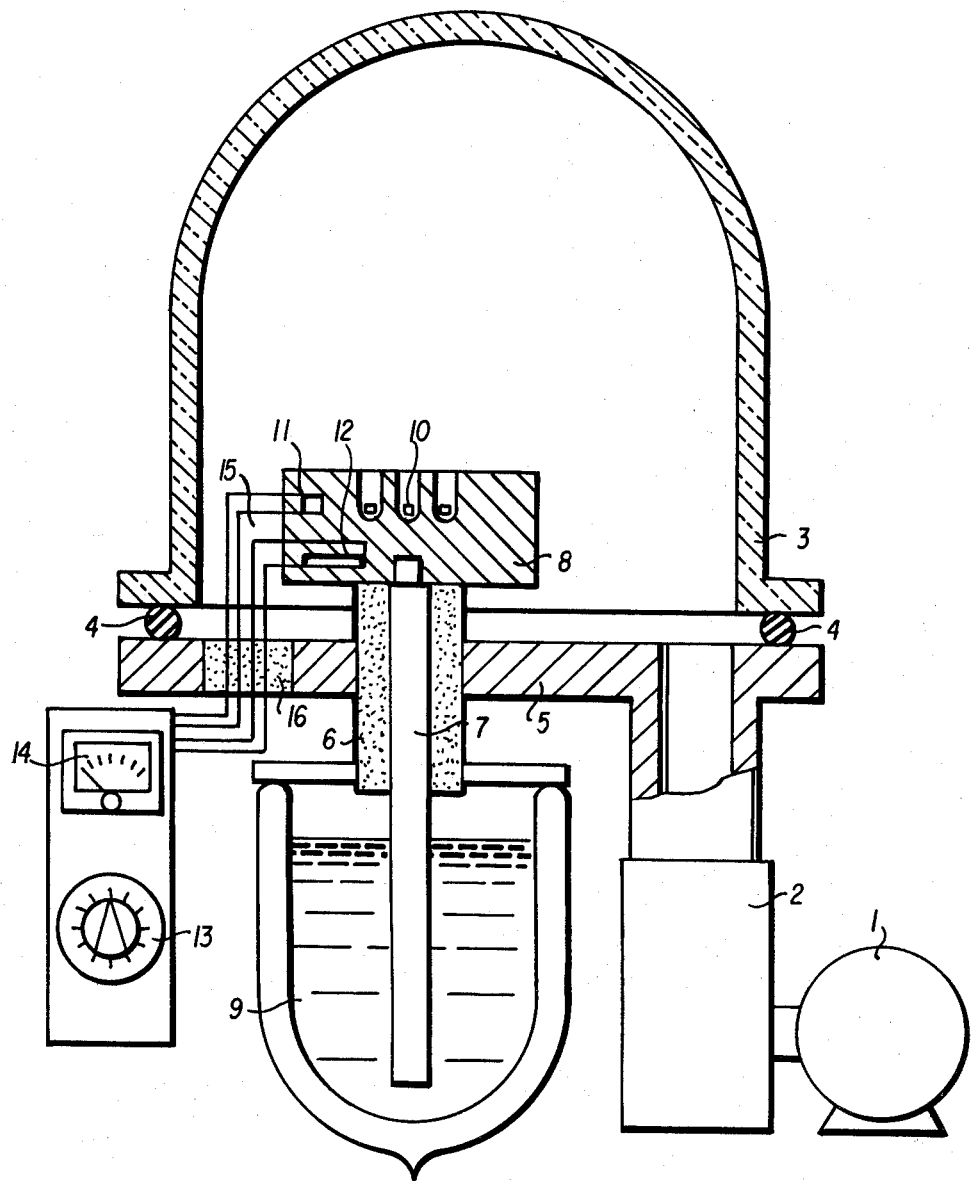

An ordinary device of the type described above, which is intended for work with light microscopes, particularly histochemical work, is illustrated in one embodiment in FIG. 1. According to this, the device consists of a high vacuum unit, which for example, is constructed of a rotary pump 1 and an oil diffusion pump 2, as well as a container 3, which lies on a bottom plate 5, with a vacuum tight seal through a gasket 4. A metal rod 7 is introduced into the container 3 through a sealing element 6, which rod is fastened to the sample holder or tray 8. The metal rod 7 is cooled by a cooling liquid 9, e.g., liquid nitrogen ($N_2$) or a solid coolant, e.g., solid carbon dioxide, or even by a cooling mixture (e.g., ice-water-$CaCl_2$ or alcohol-Dry Ice) as coolant (so-called "Cryogen"). The objects 10 composing the samples are normally held at a constant selectable temperature by an electrical control circuit. The control circuit contains among other things, a temperature sensor 11, a heating element 12, a setting device 13, and a temperature indicator 14, where connecting cables 15 are introduced through the bottom plate 5 into the container 3 by means of a vacuum-tight conduit 16. Devices of this type permit the drying of samples in sizes between approximately 10 and a maximum of 1000 mm$^3$ at temperatures between approximately $-20$ and $-50°$ C. for histological and/or histochemical purposes, where the high vacuum generated also makes possible a sublimation of the ice from the frozen biological material sufficiently rapidly for practice, at the strongly reduced water vapor pressure (water content as a rule above 90%). After this freeze drying, the objects 10 are generally transferred into molten paraffin, and sliced on microtomes after hardening of the parrafin melt (slice thicknesses approximately 1 to 20 $\mu m$). The slices produced are dyed and/or treated histochemically and subsequently examined under the light microscope.

After the introduction of the high resolution electron microscope, many attempts were made to use ordinary freeze drying devices of the type described for the freeze drying of biological objects for subsequent electron microscopic examination. It was found in these attempts that these devices did not completely meet the different requirements of electron microscopy. On the one hand, the objects for electron microscopic examination, both with respect to pretreatment ("Cryo fixation") and to post treatment (embedment in synthetic resin and dissection into ultra thin slices with thicknesses below 0.2 $\mu m$), as a rule have volumes of less than 10 mm$^3$ (normally approximately 1 mm$^3$). The amount of the ice to be vaporized is considerably smaller for that reason, than in the case of specimens for work with the light microscope. On the other hand, as a result of the resolution of the electron microscope which is higher by two powers of 10, considerably higher demands are placed on the quality of the freeze-dried specimen. Thus, for example, the deposits of pump fluid (for example, diffusion pump oil) interfere with the specimen to a considerable extent. In addition to this, considering the required complete blocking of various enzymatically catalyzed, strongly exothermic biochemical reactions for the purpose of obtaining a reliable stabilization of the ultra structure in the macromolecular region, considerably lower drying temperatures in the range of about $-80°$ C. are required. The vapor pressure of the ice contained in the object is so sharply reduced in this way, that in spite of the small size of the sample, very long drying times are required, which lie between two days as a minimum and several weeks, depending on the specimen and the specific cooling conditions. It is to be expected in this connection, that in the future lower temperatures will be used for drying, so that this problem will become even more accentuated.

Liquid nitrogen is the preferred cryogen for cooling the samples to the low temperature region. In the customary apparatus, for example, according to FIG. 1, not only the large consumption of cryogen is troubling in this respect (at least 5 L of liquid nitrogen per day—(in the general case more than 10 L of liquid nitrogen per day), but also the constant refilling of the cryogen, which must be guaranteed even over the weekends. An automated refilling adds a high cost of equipment to the already high costs of cryogen—aside from the risk of breakdown of this type of cryogen refilling equipment.

The purpose of this invention is to make possible the freeze drying of small biological samples with an individual volume of less than 10 mm$^3$ for subsequent electron microscopic examination with a simple device, which is less expensive in the manufacture or purchase, as well as simpler and more dependable in handling, and with drastically reduced operating costs (lower consumption of cryogen), does not show the disadvantages which arise from the condensation of pumping fluids of the high vacuum equipment onto the object.

This is realized according to the invention by providing that the sample tray is located in the interior and in poor heat-conducting contact with the inner walls of a submersible device which can be evacuated, which can be introduced into a Dewar flask filled with the cooling liquid in such a way that the major portion of the surface of the submersible device is in direct contact with the cooling liquid.

The device according to the invention has a series of important advantages compared with the known devices for freeze drying: the construction of the device is simple and involves only small costs of manufacture. The consumption of cryogen is so low that it is scarcely higher than the normal evaporation rate of the cryogen without the submersible device immersed in it. As a result of this low consumption of cryogen, an unsupervised operation of the device for several days up to a week is possible, depending on the sample temperature and the content of the Dewar flask. Furthermore, the device according to the invention has a maximum water vapor cryopumping capacity of the extremely cold inner wall of the submersible device, so that no back diffusion of water molecules takes place into the object. Also, an operation of the device without a pump assembly is possible by the use of a molecular sieve, and there is no problem at all in installing absolutely reproducible drying conditions through programmed temperature/time cycles, electrically controlled as required.

In contrast to the cooling principle in the known devices, no direct heat-conducting connection is made between the sample tray and the cooling liquid in the invention. Rather, the cooling tray is in poor heat-conducting contact with the inner wall of the submersible device, from which the low evaporation rate of the cryogen results. Nevertheless, it is possible to produce the desired low temperatures of the object, since the submersible device is in direct contact with the cryogen over the major portion of its outer surface.

According to an advantageous development of the invention, it is provided that the submersible device consists of at least two separable components which are mutually sealed from one another through a gasket, which can be pressed together by means of a threaded ring and are secured against rotation relative to one another. Because of the ability to disassemble the submersible device, it is possible on the one hand, to charge the sample tray with the objects, and on the other hand to keep a feeding neck through which run the electrical leads for the heat regulating circuit and the like, so small that the heat cnduction into the cryogen remains small.

With particular advantage, the sample tray is connected with the submersible device interchangeably, by means of a rapid connector. An electrical contact plug serves rather suitably as a rapid connector, through the sample tray can be heated electrically and can be adjusted in its temperature. It is to be understood that the contact plug is fastened by means of a holder, which consists also of a poorly heat-conducting material.

According to another version of the invention, it is provided that the recess or the several recesses in the sample tray is or are also formed to accept a solidified synthetic resin monomer so that the synthetic resin impregnation of the object can also take place with the drying.

Figure 2:
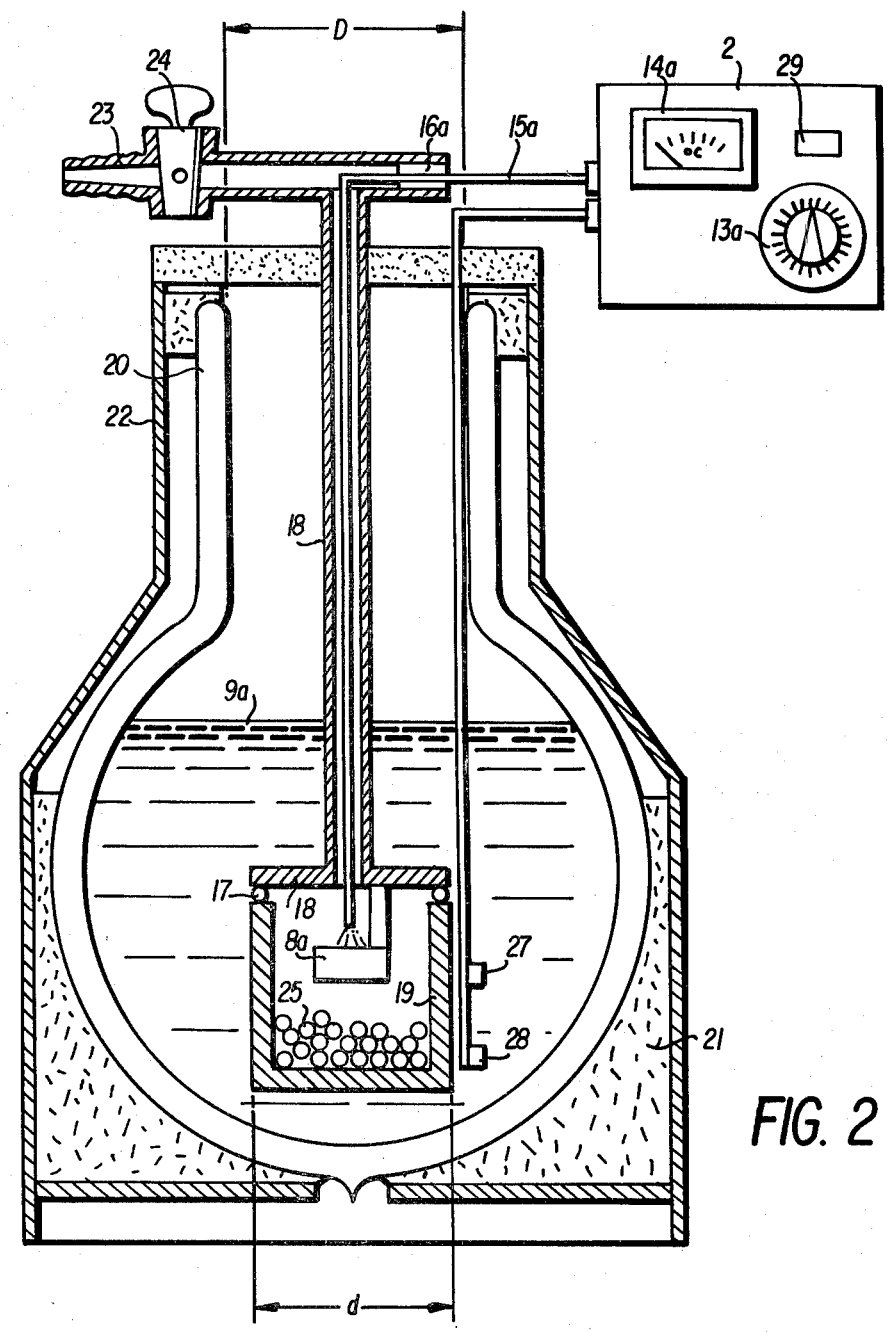

Other advantages and characteristics of the invention will become apparent from the following description of preferred embodiments, with use of the attached drawings, and also from further sub-claims. The drawings show:

FIG. 1. A schematic section through a known device for freeze drying;

FIG. 2. A schematic section through a device for freeze drying according to the invention; and FIGS. 3, 4. Modified embodiment examples of the submersible device used in the device according to the invention, on an enlarged scale.

The known device for freeze drying according to FIG. 1 has already been described in the introduction.

The device according to the invention, as is apparent from FIG. 2, comprises essentially a hollow metallic submersible device consisting of two components 18, 19, whose diameter d lies below the neck diameter D of a customary and commercial Dewar flask 20. The Dewar flask 20, by way of example, is a double walled glass flask, which is set in a metallic container 22 through an intermediate layer 21, and can be introduced into the container from above without difficulty.

Part 18 of the submersible device is formed as an extended tubelike neck, through which multiwire electrical leads 15a can be led for the temperature regulation of the sample tray 8a fastened to the part 18. The conductors 15a penetrate a vacuum-tight duct 16a into the submersible device component 18. The interior of the submersible device can be evacuated through a hose connector 23 and a valve 24.

There is no direct mechanical contact between the sample tray 8a and the submersible device component 19. Rather, the sample tray 8a is connected with the inner wall of the submersible device component 19 with the idea of the smallest possible heat conduction, so that the heat exchange surface between the component 19 and the cryogen 9a considerably exceeds that between the submersible device component 18 and the cryogen 9a. The heat transfer between the component 19 and the same tray 8a is kept as low as possible by interposition of insulating material.

It is particularly suitable to especially adapt the vacuum seal 17 between the components 18 and 19 to operation at the lowest temperatures below −150° C., by providing that metal gaskets 17b are used and are durably sealed by special arrangements - for example according to FIGS. 3 or 4.

Figure 3:
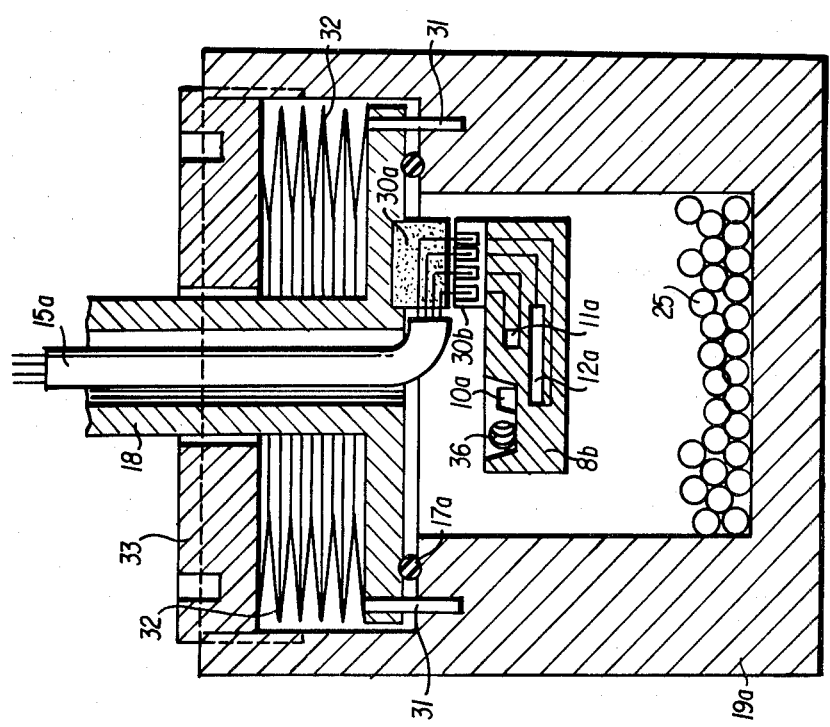

An advantageous configuration of the invention consists, according to FIG. 3, in that the sample tray 8a is connected through a contact plug with the component 18a and can be removed from this or exchanged for another in the most simple way. Furthermore, a vacuum can be generated and/or maintained in a known way, by way of another development, by introduction of a molecular sieve 25 into the cavity of the submersible device. A further advantageous development of the invention consists of providing, also in a known manner, a manual, semi- or fully automatic time control of the temperature of the sample tray by means of a regulating unit 26, which permits the temperature to be raised according to a prescribed temperature/time program, and which thereby permits impregnation of the object 10a with synthetic resin monomer. Finally, another desirable development consists of providing a level indicator for the cryogen supply 9a in the Dewar flask, which comprises at least two sensors 27 and 28 and an optical warning indicator 29 and/or an acoustic warning device, to call attention to the approaching or existing deficiency of cooling as a result of the lowering of the cryogen level.

Figure 4:
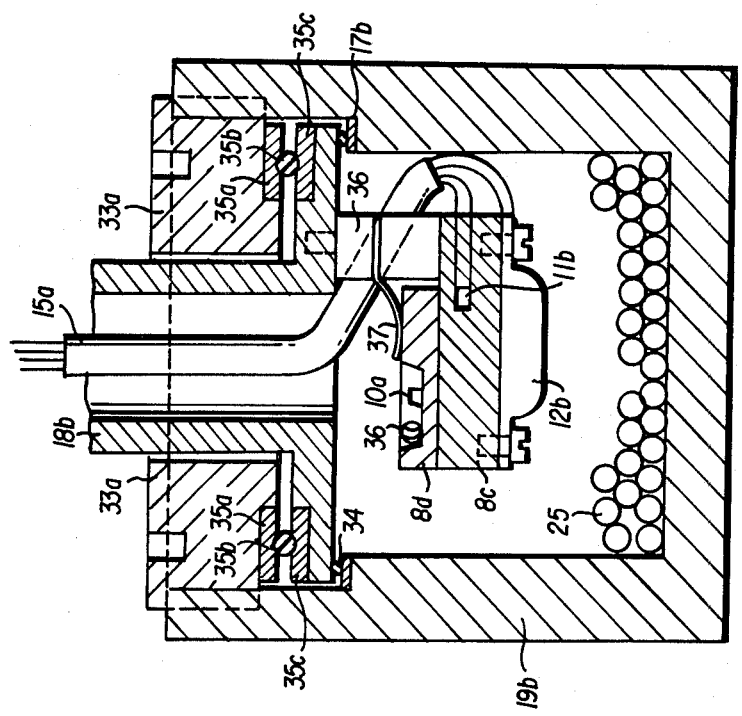

FIGS. 3 and 4 show special variations of embodiments of the submersible device. It is decisive that in the system according to the invention, only a very small heat exchange takes place between the heated sample tray 8a and the cryogen 9a, which is limited essentially to the direct solid contact through the leads 15a to the sensor 11a and the heating element 12a, and if necessary the plug connection 30a/30b, but which is completely sufficient for cooling the sample tray in view of the temperature difference between the sample tray 8a and the cryogen 9a (−80° C./−196° C. when liquid nitrogen is used). The heat exchange through the gas phase, in view of the vacuum in the submersible device, plays only a subordinate role and that only by way of heat radiation, and can be further reduced by additional measures. In this way, it is possible to keep the heating capacity of the heating element 12a for the additional consumption of cryogen caused by the heating in the use of liquid nitrogen and an object temperature between −80° and −40° C., below 0.5 L of the liquid nitrogen per day. It is important for this low heat exchange or cryogen consumption that the heat exchange surface between cryogen 9a and component 18 be kept as small as possible in comparison to that with component 19. The size of the exchange surface on component 19 is decisive for the cryogen action for water vapor, which is increased considerably by the use of a molecular sieve (e.p. Xeolite 13X).

The lead-in tube to component 18, also cooled, serves as a simple cold trap for pump fluid, as long as the freeze drying is carried out under constant vacuum. With exclusive use of a molecular sieve, however, a sufficient vacuum for the freeze drying (total pressure below $10^{-2}$ Torr, water vapor, partial pressure correspondingly lower), is obtained in a still simpler way without use of the vacuum equipment.

Of great importance is a durable vacuum-tight seal of the submersible device, which is retained even at temperatures below −150° C. over periods of time of several weeks. In accordance with FIG. 3, a seal of this type is obtained by using an O-ring 30a of suitable material, for example, in such a way that the tray-like formed foot of the component 18a, secured against rotation by the pins 31, is pressed against the component 19a through a set of tray springs 32 by means of the threaded ring 33. The spring force of the tray springs in this case guarantees a durable positive closing contact of the components 18a, 17a, 19a.

Another variety of embodiment of the seal according to the invention is shown in FIG. 4. In this case, an annular knife edge 34 encircling component 18b presses into a sealing ring 17b of a soft metal, and thereby guarantees a trouble-free permanent seal. The impression again can alternatively take place through a compression roller bearing 35 by means of the threaded ring 33a, which presses the upper bearing ring 35a through the balls 35b to the lower bearing ring 35c resting on the tray foot of the component 18b, and keeps the steel balls in shape by elastic deformation.

The electrical connection and the arrangement of the sample tray 8 play an important role in connection with the consumption of cryogen and a simple handling method. According to FIG. 3, the sample tray with the temperature sensor 11a and the heating element 12a can be connected to the base portion of element 18a through an electrical contact plug 30a/30b—for example, with corrosion resistant gold contacts. The easy plugging in and unplugging of the tray 8b makes possible a simple cleaning, loading, and removal of the object. By use of good heat insulating materials for the components 30a and 30b of the contact plug, the heat transfer from part 8b to part 18a is limited to a minimum. For purposes of impregnation, an appropriate amount of solidified synthetic resin monomer 36 can be placed in recesses especially provided for this purpose beside the frozen object 10a. After conclusion of the freeze drying, the sample tray can be heated up to such an extent by means of the heating element that the monomer becomes liquid and impregnates the sample. Thereafter, the submersible device is filled with gas through the valve 24, e.g., dry pure nitrogen. With this, the necessary steps are completed for the synthetic resin imbedment of the object 10a.

According to FIG. 4, in another variety of embodiment, a two-part sample tray 8c/8d is provided. The element 8c contains the solidly electrically wired elements 11b and 12b, and is connected rigidly through a thermally insulating intermediate piece 36 with the base of the component 18b. In this case, for cryotechnological and vacuum technological reasons, the use of a completely encapsulated high power transistor instead of a standard heating resistor is of particular advantage. The high power transistor 12b in this case can be fastened, for example, to the bottom surface of the tray 8c. The element 8d is laid on the component 8c. Good thermal contact is guaranteed by an exactly planar shaping of the corresponding contact surfaces, as well as for example, by a spring 37. It is possible both in the sample arrangement according to FIG. 3, as well as according to FIG. 4, to provide different sample trays 8b or 8d, and to exchange them rapidly with one another as required.

The device described with the use of FIGS. 2 to 4 can be realized in various variations and combinations. Thus, for example, it is possible to combine various individual features of FIG. 3 and FIG. 4, to provide the inner surface of component 19 with a profiled surface to increase the cryopumping capacity, to construct the surfaces of the various parts as an example either highly polished or dull black for the purpose of an increased or reduced heat exchange, or to provide them with a synthetic coating (e.g. poly(tetrafluoroethylene) for purposes of simplified cleaning or for removal of ice deposits. In the same way, it is unimportant in what way the electrical regulating unit 26 or a level indicator 27, 28, 29 is installed and wired, or how it operates. Also unimportant is the shape (hollow sphere or cylinder) and the execution (evacuated and mirrored double-walled glass flask; plastic foam; metal container, etc.) of the Dewar flask for the cryogen, as well as the form of the vacuum connector 23, 24, of the electrical connector 15, 16 and of the sample tray 8.

What is claimed is:

1. A device for freeze drying and synthetic resin impregnation of biological specimens which comprises a Dewar flask for holding a cooling liquid, a sealable container, support means for supporting said container in said Dewar flask below the liquid for cooling said container, valve means for connecting said container to a source of reduced pressure for evacuating said container, a sample tray having at least one recess for receiving a biological specimen, means for supporting said tray within said container spaced from the container interior and heating means for warming said tray.

2. Device according to claim 1, characterized in that the submersible sealable container comprises two separable components, a gasket (17) and can be pressed together by means a threaded ring (33, 33a), and which are secured against rotation relative to one another.

3. Device according to claim 2, characterized in that the threaded ring (33a) is supported through a pressure roller bearing (35b) on one of the sealable container components (18b) and the gasket (17b).

4. Device according to claim 2, characterized in that the gasket (17b) consists of soft metal, in which one or more gripping points (34) can be impressed.

5. Device according to one of the claims 1, 2, 3 or 4, characterized in that the sealable container contains a molecular sieve.

6. Device according to one of the claims 1, 2, 3, or 4, characterized in that the sample tray (8b) is connected exchangeably with the submersible device by means of a rapid connector.

7. Device according to claim 6, characterized in that the rapid connector is a contact plug (30a, b) through which the sample tray (8b) can be heated electrically and can be adjusted in its temperature.

8. Device according to claim 7, characterized in that the holder of the contact plug (30a, b) consists of a poor heat-conducting material.

9. Device according to one of the claims 1, 2, 3, or 4, characterized in that the recess or recesses of the sample tray (8a, b), is or are also formed to accept a solidified synthetic resin monomer (36).

10. Device according to one of the claims 1, 2, 3, or 4, characterized in that the sample tray (8c, d) consists of two components, wherein one component (8d) is connected with the upper part (18b) of the submersible device through a connecting link (36) with poor heat transfer properties, and contains a temperature sensor and a heating element, while the second component (8c) is in good heat contact with the rigidly fastened part (8d) through a flat surface, and is connected with it in an easily separable manner.

11. Device according to claim 10, characterized in that the separable component (8c) of the sample tray is subject to variable contact pressure by an adjustable assembly element.

12. Device according to one of the claims 1, 2, 3, or 4, characterized in that a device is provided in the Dewar flask (20) for monitoring the filling level of cryogen.

13. Device according to one of the claims 1, 2, 3, or 4, characterized in that a semi- or fully-automatic program control is provided for the temperature of the object as a function of time.

* * * * *